United States Patent [19]

Herr et al.

[11] 4,254,341

[45] Mar. 3, 1981

[54] RADIATION PROTECTION DEVICE, PARTICULARLY FOR MEDICAL X-RAY, RADIATION THERAPY AND DIAGNOSTIC USE

[75] Inventors: Marianne Herr, Eisenhartstrasse 27, D-8000 Müchen 60, Fed. Rep. of Germany; Stephen H. Frishauf, New York, N.Y.

[73] Assignee: Marianne Herr, Müchen, Fed. Rep. of Germany

[21] Appl. No.: 72,475

[22] Filed: Sep. 4, 1979

[30] Foreign Application Priority Data

Sep. 4, 1978 [DE] Fed. Rep. of Germany ....... 2838519

[51] Int. Cl.³ .............................................. G21F 3/02
[52] U.S. Cl. .................................... 250/519; 250/515
[58] Field of Search ....................... 250/519, 516, 515

[56] References Cited

U.S. PATENT DOCUMENTS

| | | | |
|---|---|---|---|
| 1,636,419 | 7/1927 | Hollander | 250/519 |
| 2,718,598 | 9/1955 | Graf | 250/519 |
| 2,794,128 | 5/1957 | Shasky | 250/519 |
| 3,308,297 | 3/1967 | Mansker | 250/515 |

*Primary Examiner*—Bruce C. Anderson

[57] ABSTRACT

To protect doctors and other personnel from stray radiation when using therapeutic or diagnostic X-ray or other radiation apparatus, a lead apron is suspended from a dolly or carriage rolling in a track system secured to the ceiling in which the radiation apparatus is located. The dolly or carriage can be similar to that of already existing rolling equipment. It has a centrally positioned hanger arrangement which has a turning hanger secured to the dolly to which a tension spring is attached which supports the lead apron hanger, by having attached thereto an element generally in the form of a clothes hanger from which the apron, itself, is suspended by means of an adjustable strap suspension. Preferably, an intermediate strap suspension is further interposed between the hanger and holding spring which, in turn, is supported from a swing arm attached to the dolly or carriage, the swing arm permitting lateral excursion matched preferably to the lateral swing of diagnostic apparatus, such as a fluoroscopy monitor. The spring should be sufficiently strong to support the weight of standard lead aprons with an elongation of, preferably, less than its normal, unstressed length.

10 Claims, 3 Drawing Figures

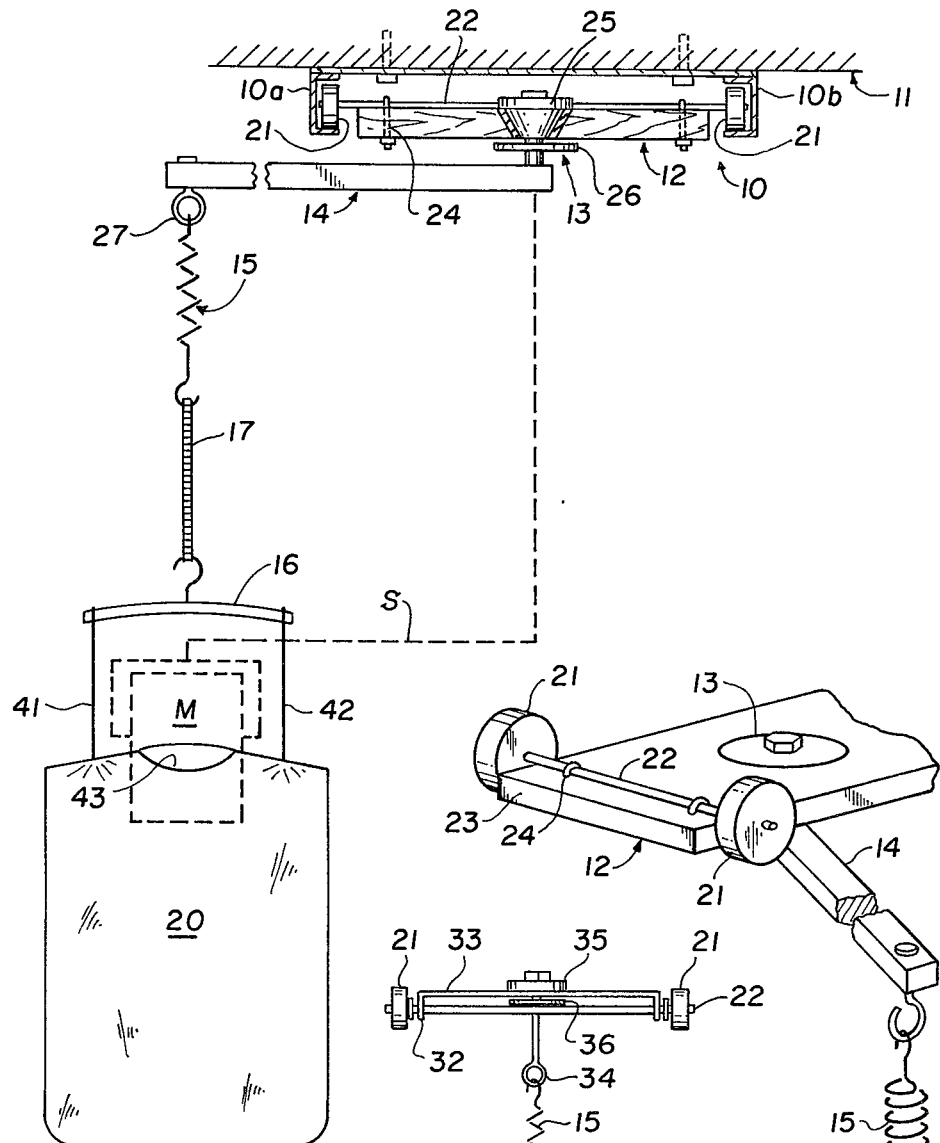
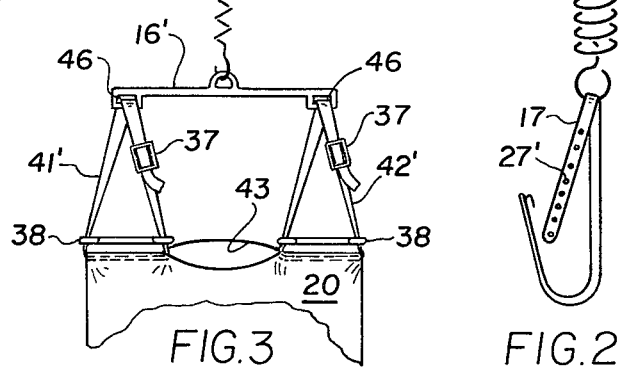
FIG.1  FIG.3  FIG.2

RADIATION PROTECTION DEVICE, PARTICULARLY FOR MEDICAL X-RAY, RADIATION THERAPY AND DIAGNOSTIC USE

The present invention relates to a radiation protection device, particularly to protect medical personnel involved in treatment and diagnosis against stray radiation which is not shielded, screened or blocked by a radiation generating apparatus, such as an X-ray fluoroscopy apparatus.

BACKGROUND AND PRIOR ART

It is known that doctors and other personnel involved in the health field should, and frequently are required, to wear lead aprons in order to protect themselves against stray radiation which is unavoidably emitted from apparatus, even when well screened. The patient who is only briefly exposed to radiation is not damaged thereby; doctors and other personnel involved in treatment and diagnosis are, however, subjected to stray radiation during the entire working time which, integrated over a long period of time, is dangerous to health. At least a portion of the stray radiation is due to the presence of the body of the patient itself within the beam of radiation so that, even if the radiation apparatus is completely shielded and screened, the doctor or other treating personnel is still exposed to stray remaining radiation. To protect themselves against stray radiation, it is customary that doctors and other personnel using radiation apparatus wear lead aprons. Such lead aprons are heavy and, if worn during an entire working day, may lead to back pain and vertebral damage. The average weight of lead aprons is between about 3 to 6 kilograms. One can readily see that wearing such a lead apron, which depends in front and in the back of the body in the form of a poncho, for a full working day is tiresome, inconvenient, and may itself lead to physical impairment.

THE INVENTION

It is an object to improve radiation protecting devices to essentially eliminate the effect of the weight of a lead apron.

Briefly, a hanger arrangement is provided which is suspended from a track secured to the ceiling of the room in which the radiation apparatus is located. The hanger arrangement includes a dolley or carriage rolling on the tracks, a turning hanger secured to the dolley, and a tension spring which supports a lead apron hanger, somewhat in the form of a clothes hanger, from which the apron itself depends, supported by ropes, belts, webs, straps, or the like, and secured to the lead apron in the region of the shoulder position thereof.

In accordance with a feature of the invention, the rotary arrangement may include a laterally projecting extension arm from which the apron itself is suspended. The laterally extending suspension arm preferably has its length and swing radius matched to the length and swing radius of diagnostic equipment, so that personnel wearing the apron can readily follow such diagnostic equipment and the excursions thereof based on the suspension of the diagnostic equipment itself.

The radiation protection device permits suspending a lead apron which may even be heavier than customarily used lead aprons, thereby affording better radiation protection, without loading the personnel carrying out diagnosis or radiation therapy. The suspension preferably is so arranged that it is longitudinally adjustable so that it can match the size of the doctor or other personnel using the protective device. The adjustment and the spring constants can be so selected that the load which remains on the shoulder of the treating or diagnostic personnel becomes a minimum, just enough so that the apron will fit well against the body of the operator without placing a substantial load or weight thereon. A remaining weight, not accepted by the spring, of from about 1/10 to ¼ kg is easily acceptable. Preferably, the suspension can be so adjusted that, selectively, no remaining weight at all is left and the apron is entirely carried by its suspension, or may even be lifted off the shoulder of the operator.

Drawings, illustrating preferred examples:

FIG. 1 is a schematic cross-sectional view through a radiation protection suspension having a swing arm;

FIG. 2 is a highly schematic perspective fragmentary view of a dolly with an apron suspension, from which the apron and the coat hanger-like suspension has been omitted in order to illustrate an adjustable hanging web; and FIG. 3 is a schematic front view of another embodiment of a dolly and another embodiment of the suspension for the apron.

A track arrangement 10, formed of two U-tracks 10a, 10b, is secured by means of bolts on a ceiling 11. The U-tracks can be maintained in suitably spaced relation by welded cross strips, or the like. A dolly 12 has four wheels 21. The four wheels 21 run on two shafts 22 which are secured to a wood plate 23 (FIGS. 1, 2) or to a steel frame 33 (FIG. 3). When the dolly itself is made of a wood plate, shaft 22 can be easily secured thereto by U-clamps 24.

The apron suspension has a rotary suspension 13, for example a tapered roller bearing 25, or a suspension roller bearing 35 (FIG. 3), preferably with a lower cover plate 26 (FIG. 1), 36 (FIG. 3), covering the bearing. A swinging arm 14 (FIGS. 1, 2) is secured to the center pin of the bearing. The free end of the swinging arm 14 carries a rotatable suspension eye 27 into which a tension spring 15 is hooked. The lower end of the tension spring 15 carries a strap 17, preferably a web of nylon, some other man-made fiber, cotton, or a mixture of cotton with nylon or other plastic fibers. The strap 17 has a plurality of holes 27' into which a hook at the other end thereof can be hooked, so that the effective length of the web or strap 17 can be adjusted (FIG. 2). A hanger 16, similar to a clothes hanger, is hooked into the lower loop of the strap 17. Two further straps 41, 42, preferably also longitudinally adjustable, depend from the outer edges of the hanger support 16. Straps 41, 42 may be adjustable by means of a buckle. The straps are attached to the shoulder region of lead apron 20. The distance between the straps 41, 42 should be wide enough so that the head of the operator can easily pass through the opening 43 of the apron and be clear of the straps.

The radiation protection device is personal to the operator. It is particularly suitable for use with fluoroscopy apparatus in which an image intensifier monitor screen M is secured to a swing arm S, and longitudinally movable in the track 10. The length of the swing arm 14 is preferably matched to the swinging excursion of the support arm for the fluoroscopy monitor, so that lateral strain and pull on the spring is avoided; such lateral pull may be annoying or inconvenient for the doctor or other personnel using the radiation apparatus with which the lead apron is to be used.

FIG. 3 shows two modifications:

In case the fluorescent monitor has only a short swinging arm, or if the swinging arm is not considered necessary, the suspension can be simplified by securing the eye 34 directly by means of bearing 35 on the dolly 12.

Different suspension for the apron 20: Two straps 41', 42' are threaded through wide, flat eyes 46 of a cross bar 16' which is hooked into spring 15, and then threaded through the head opening 43 and out at the shoulder opening of the apron 20. Spreader elements 38, approximately of the same width as the shoulder portions of the apron, prevent deformation of the apron. The straps 41', 42' are secured together into an endless loop by buckles 37.

Many changes are possible; for example, the straps or webs can be replaced by ropes, the hook suspension as clearly shown in FIG. 2 can be replaced by an infinitely adjustable buckle, the central suspension can be differently constructed than in the form of roller bearing 25 or ball bearing 35. It is important to so match the support strength of the spring in connection with the length of the strap 17 that the weight of the lead apron 20 is practically entirely accepted thereby without excessive stretch of the spring, the spring, however, still retaining enough elasticity in order to give the doctor or other operating personnel enough freedom and possibility of lateral excursion with respect to the vertical suspension. For a 4 kg lead apron, a spring of about 45 cm normal length, which stretches under weight of the apron to about 75 cm, is well suited.

The tracks, of course, can be constructed differently, for example one or two I-rails which are secured to the ceiling, on which the roller suspension slides in form of a suspension transport system. Many X-ray installation already have tracks present. The roller suspension in which the turning apron suspension is secured can then be constructed similarly to the suspension for such apparatus which runs in the tracks which are already present.

The monitor M and its swing arm S are shown schematically and in broken lines, since they form no part of the present invention. They are illustrated to show the match of arm 14 to monitor arm S.

We claim:

1. Personal radiation protection device, particularly for X-ray and radiation therapy and diagnosis, in which X-ray or radiation apparatus is installed in a room, and in which a lead apron (20) is worn by the operator personally to protect the operator from radiation,
wherein the improvement comprises
a track system (10) secured to the ceiling of the room;
a roller suspension dolly or carriage (12) rolling on and suspended in the track system;
a clothes hanger-like apron suspension (16) suspended from the dolly and moving with the dolly upon rolling movement of the dolly on the track system;
suspension means (41, 42; 41', 42') suspending the apron (20) in its shoulder region from the clothes hanger-like apron suspension (16);
and means resiliently suspending the clothes hanger-like apron suspension from the dolly (12) including
a tension spring (15) and
a rotary suspension support (13; 14, 27; 34, 35, 36) secured to the dolly or carriage.

2. Radiation protection device according to claim 1, wherein the rotary suspension support includes a swinging arm (14) secured to the dolly or carriage (12).

3. Radiation protection device according to claim 1, wherein the spring has a carrying force which is approximately matched to the weight of the apron (20).

4. Radiation protection device according to claim 1, further including an intermediate length-adjustable suspension element (17) interposed between the spring (15) and the clothes hanger-like apron suspension (16).

5. Radiation protection device according to claim 1, wherein the suspension means includes at least one of: ropes, webs, straps, belts, of nylon, cotton, or artificial fiber-cotton mixtures.

6. Radiation protection device according to claim 1, wherein the track system (10) includes a pair of U-tracks, secured to the ceiling of the room with the open portion of the U facing each other, one leg of the U of each one of the tracks being positioned adjacent the ceiling of the room;
and wherein the dolly or carriage (12) comprises an elongated plate (22) having wheels (21) laterally fitting into the open U-tracks and engaged therein.

7. Radiation protection device according to claim 1, for use in combination with a fluoroscopy monitor (M) having a laterally deflecting swing arm (S) on which the monitor is secured, and suspended in rolling suspension from said track system,
wherein the rotary suspension support includes a swinging arm (14) secured to the dolly or carriage (12), the length of the swinging arm (14) being approximately matched to the laterally deflecting swing arm (S) of the monitor.

8. Radiation protection device according to claim 1, wherein the suspension means suspending the apron from the clothes hanger-like suspension are longitudinally adjustable.

9. Radiation protection device according to claim 1, wherein the spring has a carrying force which is approximately matched to the weight of the apron (20);
the track system (10) includes a pair of U-tracks, secured to the ceiling to face each other with the open portion of the U facing each other, one leg of the U of each one of the tracks being positioned adjacent the ceiling of the room;
wherein the dolly or carriage (12) comprises an elongated plate (22) having wheels (21) laterally fitting into the open U-tracks and engaged therein;
and wherein the suspension means suspending the apron from the clothes hanger-like suspension are longitudinally adjustable.

10. Radiation protection device according to claim 9, for use in combination with a fluoroscopy monitor (M) having a laterally deflecting swing arm (S) on which the monitor is secured, and separately suspended in rolling suspension from said track system,
wherein the rotary suspension support includes a swinging arm (14) secured to the dolly or carriage (12), the length of the swinging arm (14) being approximately matched to the laterally deflecting swing arm (S) of the monitor.

* * * * *